United States Patent [19]

Matusik et al.

[11] Patent Number: 4,488,427
[45] Date of Patent: Dec. 18, 1984

[54] ROTATIONAL VIBRATORY VISCOMETER TRANSDUCER AND CIRCUIT

[75] Inventors: Frank J. Matusik, Piscataway; Donald W. Nelson, Voorhees, both of N.J.

[73] Assignee: National Metal and Refining Company, Ltd., Edison, N.J.

[21] Appl. No.: 483,142

[22] Filed: Apr. 8, 1983

[51] Int. Cl.³ .......................................... G01N 11/16
[52] U.S. Cl. ........................................................ 73/59
[58] Field of Search .................................... 73/59, 54

[56] References Cited

U.S. PATENT DOCUMENTS

| | | | |
|---|---|---|---|
| 3,382,706 | 5/1968 | Fitzgerald et al. | 73/59 |
| 3,710,614 | 1/1973 | Oppliger | 73/59 |
| 3,712,117 | 1/1973 | Fitzgerald et al. | 73/59 |
| 3,762,429 | 10/1973 | Fitzgerald et al. | 137/92 |

Primary Examiner—Anthony V. Ciarlante
Attorney, Agent, or Firm—Arthur L. Lessler

[57] ABSTRACT

A torsional mode rotational vibratory viscometer having an elastic hollow metal sheath extending below a support plate and secured to the plate by a weld. A rigid rod is disposed within the sheath and welded to the lower end of the sheath. An immersible tip is also secured to the lower end of the sheath. The free upper end of the rod extends above the support plate. A crossbar with ends of magnetically permeable material is secured to the free end of the rod and is caused to oscillate by a magnetic drive coil adjacent one end of the crossbar. Prior to mounting of the crossbar, the assembly is subjected to a specific heat treating schedule. A magnetic detector coil adjacent the other end of the crossbar detects the angular oscillation of the rod. Circuitry connected to the coils maintains the amplitude of oscillation of the rod constant. When the tip is immersed in a fluid, the power supplied to the drive coil is determined by the circuit and is a measure of the viscosity-density product of the fluid. The circuitry includes a sample-and-hold circuit having a clipping level which varies with the detector coil signal level, and a variable exponent amplifier to accurately correct for deviation of the drive coil current-power relationship from a square function.

20 Claims, 5 Drawing Figures

FIG. 1
FIG. 2
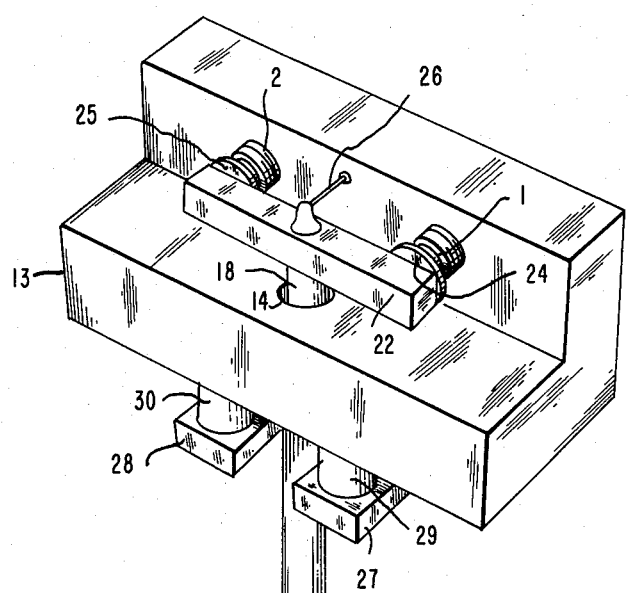
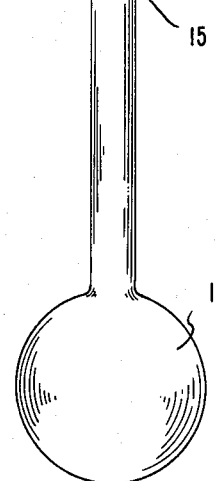
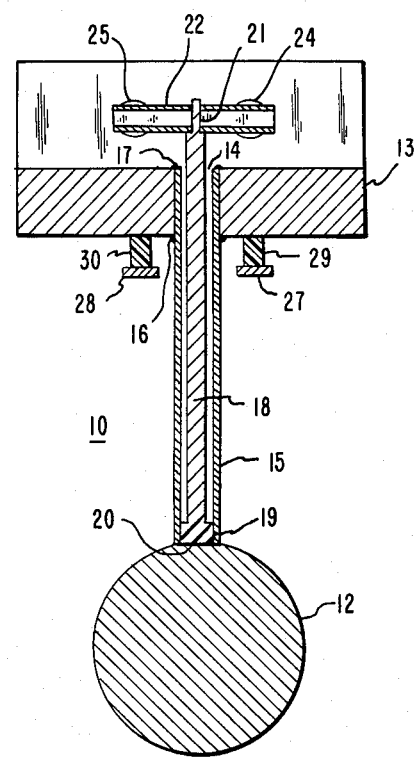

ROTATIONAL VIBRATORY VISCOMETER TRANSDUCER AND CIRCUIT

BACKGROUND OF THE INVENTION

This invention relates to an improved rotational vibratory viscometer transducer and circuit, for measuring the viscosity of fluids.

Rotational vibratory viscometers are well known in the art, and generally comprise (i) a transducer having a tip immersible in a fluid the viscosity of which is to be determined, (ii) an electromagnetic drive coil for causing the tip to rotationally oscillate with a very small angular amplitude, (iii) a feedback control circuit for maintaining the angular amplitude of oscillation of the tip at a predetermined constant value irrespective of the viscosity of the fluid, and (iv) a circuit for determining the power supplied to the drive coil, usually by squaring the current supplied to said coil, which power is a measure of the viscosity of the fluid.

A viscometer of this type is described, for example, in "Viscometer for Energy Saving", J. V. Fitzgerald, F. J. Matusik, and P. C. Scarna, Jr., Measurements & Control, April 1980. Similar viscometers are described in the references cited in said article, as well as in U.S. Pat. Nos. 3,382,706; 3,710,614; 3,712,117; 3,762,429; 3,875,791; and 4,299,119.

In the commercial use of such viscometers difficulties have been encountered in the manufacture of the transducers and in the stability of the zero adjustment of the instruments.

In manufacturing transducers of the type shown, for example, in FIGS. 1 and 2 of U.S. Pat. No. 3,382,706, approximately 50% of the transducers had to be discarded or remanufactured because they would not oscillate consistently in conjunction with the associated control circuit. The vibratory characteristics of the transducers varied widely from one unit to the next, although all units were made with the same materials and dimensions.

In using those transducers which oscillate properly, the usual procedure is to calibrate the instrument by setting the output thereof to zero with the tip oscillating in air or vacuum (to compensate for internal energy losses in the transducer). However, this zero setting tended to drift with time at a troublesome rate, and to vary substantially with temperature, necessitating frequent readjustment of the instrument (typically at intervals on the order of 15 minutes). As a result, such instruments have been virtually unusable for remote on-line monitoring of the viscosity of fluids in process control applications.

Accordingly, an object of the present invention is to provide an improved rotary vibratory viscometer transducer exhibiting greater manufacturability and operational stability than similar prior art transducers, and an improved circuit for use in conjunction therewith.

SUMMARY OF THE INVENTION

As herein described, according to one aspect of the invention there is provided a transducer assembly for a torsional mode rotational vibratory viscometer, comprising: a metal support plate having a hole extending through the plate; a hollow cylindrical metal sheath having torsional elasticity, the outer surface of an upper end part of said sheath being secured to said plate at said hole by a metal weld, so that said sheath is substantially coaxial with said hole; an immersible tip member secured to a lower end part of said sheath below said plate; a rigid cylindrical metal rod disposed within, spaced from and substantially coaxial with said sheath, a lower end part of said rod being secured to the lower end part of said sheath by a metal weld; said rod extending through said hole and having an upper end above said plate; and a metal crossbar secured to the upper end of said rod, said crossbar comprising magnetically permeable means.

According to another aspect of the invention there is provided a method for manufacturing a transducer assembly for a torsional mode rotational vibratory viscometer, comprising the steps of: providing a metal support plate having a hole extending through the plate; providing a hollow cylindrical metal sheath having torsional elasticity; welding the outer surface of an upper end part of said sheath to said plate at said hole, so that said sheath is substantially coaxial with said hole; securing an immersible tip member to a lower end part of said sheath below said plate; providing a rigid cylindrical metal rod disposed within, spaced from and substantially coaxial with said sheath; welding a lower end part of said rod to the lower end part of said sheath, so that said rod extends through said hole and has an upper end above said plate; and securing a metal crossbar comprising magnetically permeable material to the upper end of said rod.

According to a further aspect of the invention there is provided a rotational vibratory viscometer transducer and circuit, comprising: a transducer assembly comprising: a metal support plate having a hole extending through the plate, a hollow cylindrical metal sheath having torsional elasticity, the outer surface of an upper end part of said sheath being secured to said plate so that said sheath is substantially coaxial with said hole, an immersible tip member secured to a lower end part of said sheath below said plate, a rigid cylindrical metal rod disposed within, spaced from and substantially coaxial with said sheath, a lower end part of said rod being secured to the lower end part of said sheath, said rod extending through said hole and having an upper end above said plate, and a metal crossbar secured to the upper end of said rod, said crossbar comprising magnetically permeable means; a drive coil adjacent one end of said crossbar for applying magnetic force thereto to cause rotational oscillation of said crossbar, rod, tip and sheath; a magnetic detector coil adjacent the other end of said crossbar to detect said oscillation; first circuit means connected between said coils to maintain said oscillation at substantially the natural frequency thereof and at a predetermined constant amplitude, said first circuit means including a sample-and-hole circuit for sampling an input signal corresponding to the output of said detector coil at a given part of each cycle of said oscillation, said sample-and-hold circuit including means for clipping the input signal thereto at a level proportional to the amplitude of said oscillation; and second circuit means for generating a viscosity-density product indicating signal corresponding to the power supplied to said drive coil.

According to a still further aspect of the invention there is provided a rotational vibratory viscometer transducer and circuit, comprising: a transducer assembly comprising: a metal support plate having a hole extending through the plate, a hollow cylindrical metal sheath having torsional elasticity, the outer surface of an upper end part of said sheath being secured to said plate so that said sheath is substantially coaxial with said hole, an immersible tip member secured to a lower end part of said sheath below said plate, a rigid cylindrical metal rod disposed within, spaced from and substantially coaxial with said sheath, a lower end part of said rod being secured to the lower end part of said sheath, said rod extending through said hole and having an upper end above said plate, and a metal crossbar secured to the upper end of said rod, said crossbar comprising magnetically permeable means; a drive coil adjacent one end of said crossbar for applying magnetic force thereto to cause rotational oscillation of said crossbar, rod, tip and sheath; a magnetic detector coil adjacent the other end of said crossbar to detect said oscillation; first circuit means connected between said coils to maintain said oscillation at substantially the natural frequency thereof and at a predetermined constant amplitude, said first circuit means including a sample-and-hold circuit for sampling an input signal corresponding to the output of said detector coil at a given part of each cycle of said oscillation; and second circuit means for generating a viscosity-density product indicating signal corresponding to the power supplied to said drive coil, said second circuit means including a variable exponent amplifier for converting a processed signal corresponding to the current supplied to said drive coil, to said viscosity-density product indicating signal.

IN THE DRAWING

FIG. 1 is a partially cut-away perspective view of a transducer according to a preferred embodiment of the present invention;

FIG. 2 is a front elevation cross-sectional view of said transducer;

DETAILED DESCRIPTION

Figure 3:
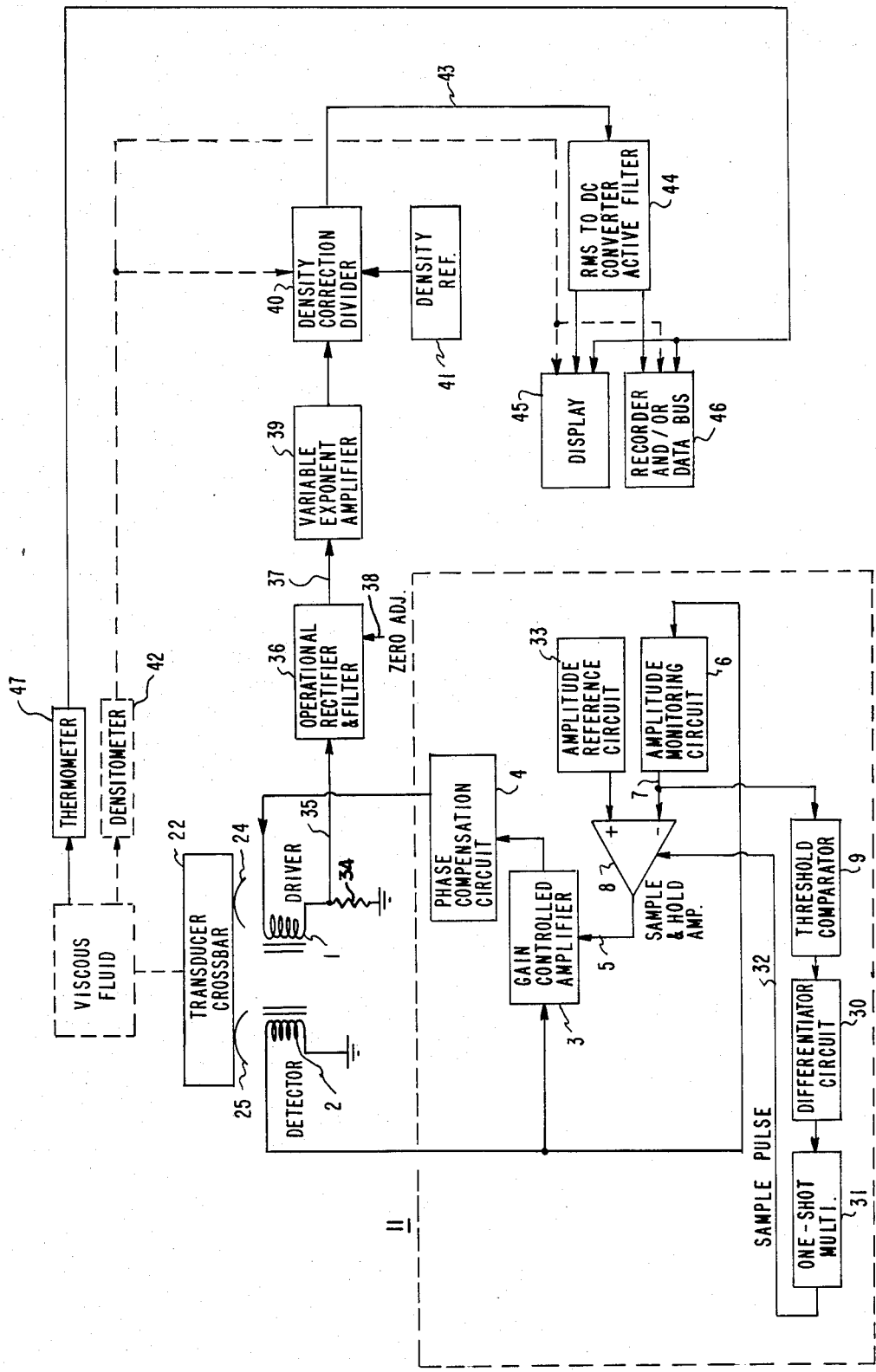
FIG. 3 is a functional block diagram of a viscometer incorporating said transducer.

The viscometer shown in the drawings consists of a transducer 10 (FIG. 1), a circuit portion 11 (shown in block diagram form in FIG. 3 and in detail in FIG. 4) for causing the transducer tip 12 to rotationally oscillate, and a circuit portion (shown as the remainder of FIG. 3, and in detail in FIG. 5) for determining the viscosity of the fluid in which the tip 12 is immersed, by processing the current supplied to the drive coil 1 of the transducer 10, the square of which current corresponds to the power supplied to said coil and to the viscosity-density product of said fluid, which power when divided by the fluid density provides the viscosity of the fluid.

TRANSDUCER ASSEMBLY

As shown in FIGS. 1 and 2, the transducer 10 consists of an L-shaped cold rolled carbon steel or type 316 stainless steel support block or plate 13 (the words block and plate being used interchangeably) having a hole 14 through it. A hollow cylindrical type 316 stainless steel sheath 15 having torsional elasticity about its longitudinal axis has an upper end extending into the hole 14, with the outer surface of said upper end being secured to the plate 13 by circular heliarc welds 16 and 17, the weld material being the same as the material of sheath 15, i.e. type 316 stainless steel.

A rigid cylindrical solid type 316 stainless steel rod 18 is disposed within, spaced from and coaxial with the sheath 15, the lower end of the rod 18 being secured to the lower end of the sheath 15 by a circular heliarc weld 19, the weld material being the same as the material of sheath 15 and rod 18, i.e. type 316 stainless steel.

The immersible tip 12 is a solid ball of type 316 stainless steel, typically having a diameter on the order of 3.2 cm., and is secured to the lower end of the rod 18 by a heliarc weld 20, the weld material being the same as the material of sheath 15, rod 18 and tip 12, i.e. type 316 stainless steel.

The upper end of the rod 18 extends through the hole 14 above the corresponding portion of the plate 13, and has a narrowed end part 21 which extends through a hole in a hollow rectangular cross-section stainless steel crossbar 22, the rod 18 being secured to the crossbar 22 by silver brazing. The crossbar 22 is made hollow to improve its strength to weight ratio.

Disk-shaped high permeability Invar magnetic pole pieces 24 and 25 having a low thermal expansion coefficient are secured to opposite ends of the crossbar 22 by silver brazing.

The crossbar 22 should be relatively non-magnetic as compared with the pole pieces 22, so that undesirable magnetic coupling between the magnetic fields through said pole pieces is minimized.

The transducer structural parts 13, 15, and 18 can be made of other materials that are mutually weldable, provided that internal stresses are subsequently relaxed by an annealing treatment. Suitable materials are invar, ordiniary steel, various types of stainless steel such as types 316, 321, 324 and 329; provided that the parts 13, 15 and 18 are properly welded together and thereafter annealed.

Anchor wire 26 is silver brazed between the upper end of rod 18 extending above the crossbar 22, and the adjacent vertically extending surface of plate 13, to stabilize the upper end of the rod 18 and prevent non-rotational oscillation thereof. After brazing, the anchor wire 26 is quenched to obtain a brittle state, which is required to minimize internal losses during operation of the transducer.

Electromagnetic drive coil 1 and detector coil 2 are mounted in the vertically extending portion of plate 13 adjacent crossbar pole pieces 24 and 25 respectively. Each of the coils 1 and 2 has a high coercivity Alnico magnetic core, eliminating need for the zero-adjusting magnet 35 required in the similar arrangement shown in FIGS. 1 and 2 of U.S. Pat. No. 3,382,706; and eliminating need for the pole pieces to be permanent magnets, as is required for the pole pieces 26 of said patent. The coils 1 and 2 are type 3015 HTB manufactured by Electro Co., Chicago, Ill. Alternatively, "Airpax" type 1-0032 coils may be used.

The transducer plate 13 is supported from brackets 27 and 28 by resilient bushings 29 and 30 respectively, to provide isolation of the transducer 10 from interference due to external vibrations.

In operation, a feedback circuit 11 (FIG. 3) having its input connected to the detector coil 2 and its output connected to the drive coil 1 causes a varying magnetic field to be applied by the drive coil 1 to the pole piece 24 to cause the crossbar 22 to rotationally oscillate about the axis of the rold 18 and sheath 15. The frequency of oscillation is the natural frequency of the transducer 10, which in the preferred embodiment is 750±15 Hz. The amplitude of oscillation is quite small, and in the preferred embodiment is such that the amplitude of movement at the surface of the tip 12, i.e. rotation about the polar axis of the tip 12, which corresponds to the longitudinal axis of the rod 18 and sheath 15, is on the order of 25 microns.

The rotational oscillation of the crossbar 22 and rod 18 results in corresponding rotational movement of the lower end of the sheath 15 and of the tip 12 secured thereto, with the upper end of the sheath 15 being held stationary by the weld 16. Thus the sheath 15 undergoes torsional deformation, with maximum torsional stress at the weld 16.

In prior art arrangements such as that shown in FIGS. 1 and 2 of U.S. Pat. No. 3,382,706, the connections between (i) the upper end of the steel sheath 32 and the transducer plate, and (ii) the lower ends of the steel sheath 32 and steel rod 28 were made by silver brazing, while the transducer tip 24 was threaded into the lower end of the rod 28 or silver brazed thereto.

In such prior art arrangements it was found that supposedly identical transducer assemblies varied in natural frequency well beyond the acceptable range, requiring such assemblies to be selected for proper natural frequency. It was also found that all such prior art transducer assemblies exhibited a high drift rate as well as a high temperature sensitivity. That is, the current drawn by the drive coil 1 was found to vary with time and the temperature of the fluid in which the tip 12 was immersed. These problems resulted in a high rejection rate of transducer assemblies, typically on the order of 50%.

The drift effect with even the best of the prior art transducer assemblies resulted in the necessity to readjust the zero setting of the viscometer (requiring removal of the tip 12 from the fluid and its placement in a reference medium such as air or vacuum) at intervals of about 15 minutes, and often required such adjustment between readings (especially when switching between high and low viscosity ranges)—making the viscometer all but useless for remote monitoring and process control applications.

On the other hand, when the aforementioned silver brazed connections were replaced by the welds 16, 17, 19 and 20 of the present invention, a dramatic improvement was realized. The resulting transducer assemblies exhibited uniform natural frequencies of rotational oscillation, well within acceptable tolerances. More importantly, the drift rates of the assemblies made according to the present invention was enormously improved, so that the viscometer required virtually no zero adjustment after initial calibration thereof, even after days of use. The resulting viscometer was virtually insensitive to temperature variations within its operating range. Internal energy losses within the oscillating transducer assembly were reduced by a factor in the range of 100 to 1,000, and said losses did not vary significantly with time or temperature. These improvements resulted in uniformly repeatable performance from transducer to transducer even when different lengths of the sheath 15 and rod 18 were utilized; and when different shapes of the tip 12, e.g. cylinder, disk, rod, etc. were employed.

When the transducer subassembly comprising plate 13, tip 12, sheath 15 and rod 18 was subjected to a specially developed heat treating schedule (before securing the crossbar 22 and anchor wire 26 to the rod 18) a further improvement was realized in reduction of drift and of temperature sensitivity. This heat treating schedule, which is described below, is substantially different from the annealing schedule normally used for the type 316 stainless steel involved, and the precise reason why the schedule given below provides improved viscometer performance is not known.

The aforementioned subassembly is heat treated by placing it on a platform having a ring of sand thereon surrounding the subassembly. A bell housing is placed over the subassembly and engages the sand ring to form a "sand lock" so that a chamber comprising the bell housing and platform and leakily sealed by the sand lock is formed.

The bell housing is equipped with a nitrogen gas inlet and a valve system to maintain and regulate the nitrogen atmosphere within the chamber, throughout the heat treating process; during which process nitrogen gas is caused to flow through the chamber at a pressure at least equal to atmospheric pressure and at a flow rate typically in the range of 25 to 60 cubic feet per minute.

The chamber is placed in a heat treating furnace which is heated to 925° F., which temperature is maintained for 3 hours. The furnace temperature is then reduced to 600° F. by turning down the furnace burners to the 600° F. setting, so that the subassembly is furnace cooled from 925° F. to 600° F.

When the 600° F. temperature is reached, the furnace burners are turned off, and the subassembly is furnace cooled to 250° F. When the 250° F. temperature is reached, the chamber is removed from the furnace, the flow of nitrogen is halted, and the subassembly is allowed to cool to room temperature. Then the bell housing is removed from the sand lock platform and the subassembly is removed for attachment of the crossbar 22 and anchor wire 26, followed by heat treating and quenching of the anchor wire as previously discussed.

The transducer assembly manufactured above exhibited performance over that of U.S. Pat. No. 3,382,706 to the extent that it can be used, for example, in the circuit arrangement shown in U.S. Pat. No. 3,710,614 without any need for the preamplifier 170 and phase adjustment network 173 thereof.

An important feature of the transducer assembly described above is the relative speed with which it can be calibrated as compared with prior art vibratory viscometer transducer assemblies. A series of transducer assemblies made according to the present invention can be consecutively calibrated by attaching them in succession to a single electronic control unit that has been preset by calibration (about 1 centipoise) in distilled water, so that calibration at this single point will result in an accuracy within ±10% over a range of $10^{-1}$ to $10^5$ centipoise. The accuracy can be brought to better than ±1% of full scale in each of the six decades by trimming while the transducer tip is successively immersed in certified NBS viscosity standard fluids. Trimming to one standard fluid in each decade range is sufficient to achieve the aforementioned 1% accuracy. This procedure (which typically takes about 2.5 hours per unit) is far simpler than that required for calibration of prior art transducer assemblies (which typically took about 6 hours per unit), and has enabled manufacture of in-line viscometers for process control applications which are as accurate as the laboratory models thereof.

SYSTEM DESCRIPTION

As best seen in FIG. 3, gain controlled amplifier 3 has its input connected to the output of detector coil 2 and its output connected through a phase compensation circuit 4 to the input of drive coil 1, to form a positive feedback loop which maintains the transducer crossbar 22 in rotational oscillation at the natural frequency thereof. The amplitude of the oscillation is maintained constant by control of the gain of amplifier 3 via a gain control signal applied thereto on line 5.

An amplitude monitoring circuit 6 has its input connected to the output of detector coil 2, and provides on its output line 7 an AC signal at the frequency of oscillation of the crossbar 22, said AC signal having an amplitude corresponding to the amplitude of oscillation of the crossbar 22.

The AC signal output of amplitude monitoring circuit 6 is applied to (i) sample-and-hold circuit 8 and (ii) threshold comparator 9. Threshold comparator 9 generates an output signal once during each cycle of the AC signal on line 7, at a time when said AC signal crosses a preset amplitude threshold, i.e. at a time when crossbar 22 is in a particular position of its cycle of rotational oscillation, preferably at or near the peak of the oscillation cycle. That is, the output signal from threshold comparator 9 always appears in successive cycles at the same physical position of the crossbar 22.

Threshold comparator 9 includes a 90° phase shift circuit to shift the AC signal on line 7 so that the zero crossovers of the phase shifted signal occur at the same times as the peaks of said AC signal on line 7. The comparator 9 then compares the phase shifted signal with ground, to generate an output signal at each positive-going (or negative-going) zero crossover.

The output of threshold comparator 9 is differentiated by differentiator circuit 30, with the output of circuit 30 being coupled to monostable multivibrator 31, which provides sampling pulses (one sampling pulse per cycle of oscillation of the crossbar 22) to the sample-and-hold circuit 8 on line 32.

The AC signal on line 7, corresponding to amplitude of oscillation of the crossbar 22, is compared by sample-and-hold circuit 8 with a DC reference signal (indicative of the desired amplitude of oscillation of the crossbar 22) provided by amplitude reference circuit 13, the comparison being made only at times corresponding to the appearance of sampling pulses on line 32.

The result of each such amplitude comparison, i.e. the amplitude error signal, is stored by sample-and-hold amplifier 8 and held at the last stored value between successive samples, so that the output of amplifier 8 is a varying DC amplitude error signal which is applied to gain controlled amplifier 3 to maintain the amplitude of rotational oscillation of the crossbar 22 (and therefore of transducer tip 12) at a predetermined constant value.

In order to prevent overloading of the sample-and-hold amplifier 8 due to transients caused, e.g., by shock to the transducer assembly 10, a clipping circuit (diodes D1 and D2 and resistors R26 and R27, FIG. 4) prevents the output of the sample-and-hold amplifier 8 from exceeding a preset value (−6 volts) in the negative direction and from rising above zero volts in the positive direction. The normal operating range of sample-and-hold amplifier 8 is −4 v. to −1.3 v. Diode D1 clamps the amplifier if its output is driven positive. This diode is also useful in clipping noise spikes which may occur. Diode D2, in conjunction with voltage dividing resistors R26 and R27, clamps the inverting input of amplifier 8 when the output of amplifier 8 is driven more negative than −6 v. This clamping arrangement provides improved response from an overload condition, when the amplifier 8 would otherwise be driven into saturation, where excessive charge time on the hold capacitor would retard the recovery of the circuit.

In remote monitoring and process control applications, the transducer 10 is often installed a considerable distance from the amplitude control circuit 11, so that the lines to the coils 1 and 2 may be rather long, with typical line lengths being as much as 350 ft. The phase shift introduced by these lines changes the loop phase shift between coils 1 and 2 (nominally 180°) required for proper oscillatory operation of the transducer 10, so that oscillation of the crossbar 22 is intermittent and, in severe cases, ceases entirely.

Figure 4:
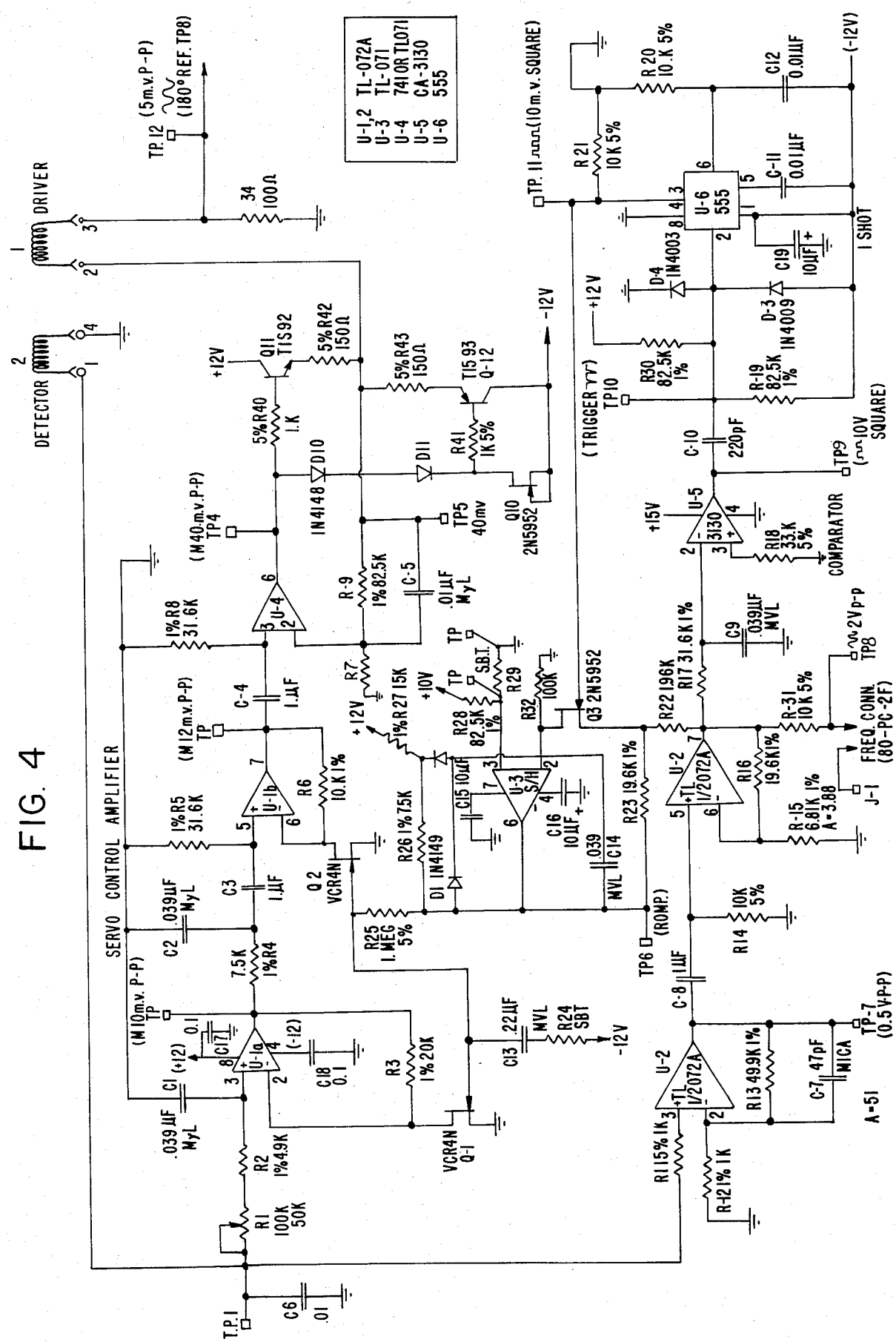
FIG. 4 is a functional schematic diagram of the portion of said viscometer that maintains a predetermined amplitude of rotational oscillation of said transducer.

To overcome this problem and enable operation with long lines between transducer 10 and control circuit 11, a phase compensation circuit 4 (resistors R1 and R2, capacitor C1 of input to amplifier U-1; resistor R4 and capacitor C2 in output circuit thereof, FIG. 4) introduces an adjustable amount of phase shift into the positive feedback loop. The phase compensation circuit 4 is adjusted so that the transducer oscillates properly with close to 180° phase shift between the drive and detector coils 1 and 2 under varying load conditions (i.e. with the tip 12 subjected to fluid viscosities in the range of 0.001 to 2,000 poise), and the viscosity output of the viscometer exhibits acceptable long term stability.

The phase compensation circuit 4 is also useful in correcting for phase shifts due to the use of long lengths of the sheath 15 and rod 18, and/or to high fluid pressures.

With the transducer 10 oscillating under control of the circuit 11, an AC signal having an amplitude nominally corresponding to the square root of the viscosity-density product of the fluid in which the tip 12 is immersed, is provided from resistor 34 on line 35, this signal corresponding to the current flowing through the drive coil 1, which is in series with resistor 34.

The AC signal on line 35 is converted to a DC signal having a value corresponding to the current through resistor 34, by operational rectifier and filter 36; the output of rectifier and filter 36 appearing on line 37, said output being shifted by a DC zero adjust level applied on line 38 to compensate for internal losses in the transducer 10, i.e. to calibrate the viscometer to zero viscosity when the tip 12 is immersed in air or vacuum.

The variable exponent amplifier 39 "squares" the output signal on line 37, since the viscosity-density product is proportional to the power supplied to the drive coil 1, which in turn is proportional to the square of the current through the coil 1 and resistor 34. In the prior art this function was provided by a squaring circuit (see, e.g., the squaring amplifier 176 of U.S. Pat. No. 3,710,614 and column 7, lines 5 to 12 et seq. thereof). However, the relationship between the signal on line 37 and viscosity-density product is not a perfect square function, so that prior art use of a squaring amplifier resulted in nonlinearities which required complex curve fitting or alignment circuits to correct.

According to the present invention the prior art squaring circuit is replaced by a variable exponent amplifier 39 having an exponent range on the order of 1.9 to 2.1. This circuit has been found to provide an excellent linearity of output of viscosity-density product, without the need for the curve fitting or alignment circuits of the prior art.

A suitable variable exponent amplifier is available from Analog Devices, Norwood, Mass., as a "Model 433 Programmable Multi-Function Module"

A density correction circuit 40 divides the viscosity-density product output of variable exponent amplifier 39 by a density signal from (i) a manual density setting reference control 41 or (ii) an optional automatic densitometer 42. The output signal from density correction circuit 40 on line 43 is then a DC signal corresponding to the viscosity of the fluid in which the transducer tip 12 is immersed. A suitable divider circuit is Analog Devices, Inc. AD 535, using two trims as described in Analog Devices Data Acquisition Products Catalog Supplement, page 59S (1979).

The viscosity output signal on line 43 is then applied to an active filter comprising RMS to DC converter 44, which accurately averages out noise due, e.g., to pipeline turbulence and other sources. Such RMS to DC converters are commercially available from various sources, including National Semiconductor Corporation and Analog Devices, Inc.

Applicants have found that the RMS to DC converter 44 works better than other types of active filters in smoothing viscosity signals. The reason for this improvement in performance is not known. In addition, the RMS to DC converter responds more quickly to changes in the viscosity signal than do other types of filters, and has less overshoot.

The viscosity signal output of the RMS to DC converter 44, is coupled to a digital display 45 and, if desired to a recorder or a data transmission bus 46. The outputs of the densitometer 42 and an optional thermometer 47 may also be coupled to the display 45 and bus 46, if so desired.

CIRCUIT DESCRIPTION

As shown in FIG. 4, operational amplifiers U1a and U1b, U4, bipolar transistors Q-11, Q-12 and field effect transistors ("FETS") Q-1, Q-2 and Q-10 with their associated circuits comprise the automatic gain controlled power amplifier 3. The power amplifier 3 with complementary symmetry output is connected to the drive coil 1 of the transducer 10.

If desired, the drive coil 1 may comprise a pair of coils disposed on opposite sides of the same end of the crossbar 22, and driven in push-pull arrangement by the complementary symmetry output of the amplifier 3.

The detector coil 2 may be similarly constructed, resulting in cancellation of common mode noise; which arrangement is particularly advantageous when the lines to the coils 1 and 2 are long.

The power amplifier stage of U-4 comprises bipolar transistors Q-11 and Q-12. The gain of U-4 is set by the ratio of R-9 and R-7. Feedback capacitor C-5 reduces amplifier gain at higher frequencies to eliminate possible harmonic oscillations of the transducer 10, particularly sheath 15 and crossbar 22, at high load conditions or when the transducer shaft length is substantially increased. Diodes D-10 and D-11 provide operating bias and temperature compensation for transistors Q-11 and Q-12 in conjunction with field effect transistor Q-10. Operating power for the complementary symmetry output is supplied via a positive DC terminal at the collector of transistor Q-11 and a negative DC terminal at the collector of transistor Q-12.

The gain control voltage of U-1a and U-1b is supplied through R-25 to the gates of field effect transistors Q-1 and Q-2. Possible parasitic oscillations of U-1a and U-1b in conjunction with Q-1 and Q-2 are eliminated by selection of resistor R24 and capacitor C-13. Gain limit setting of U-1a is achieved by resistor R-3; and for U-1b is achieved by resistor R-6. Proper gain setting provides operation in the linear range of U-1a and U-1b, and Q-1 and Q-2; and also provides compensation for inherent differences from one amplifier to another or for differences between the Q-1 and Q-2 FETs. Q-1 and Q-2 are linear control FETs, type VCR4N, made by Siliconix, Inc., Santa Clara, Calif. The use of these devices eliminates selection problems experienced with conventional FETs, which are frequently non-linear over part of the operating range. Although the whole servo amplifier system is essentially non-linear, the use of linear control elements at this point improves tracking the general operation.

The input of Q-1 and Q-2 is clamped by diode D-2 when the output of U-3 exceeds −6 volts as determined by voltage dividers R-26 and R-27. The −6 volt clamping point is sufficient for the viscometer to operate in the selected range of 0.001–2000 poise; or from 1.0 poise to 20,000 poise damping when the transducer tip is properly modified for high load applications. Diode D-1 prevents the output of U-3 from going positive. The normal range of operation for the output of U-3 is −3.6 v. for lowest gain of U-1 and −1.3 v. for highest gain of U-1.

Diodes D-1 and D-2 restrict the amplifier from latching or saturating under overload conditions; therefore, normal control conditions of the circuit are automatically restored upon termination of the overload conditions—and with a minimum of delay after such overload condition termination.

Since the gain of the operational amplifiers U-1a and U-1b is set by the ratio of feedback resistors R-3 and R-6 to the effective source-drain resistance of the junction field effect transistors Q-1 and Q-2, variations of the applied gain control voltage on the gates of Q-1 and Q-2 results in corresponding variations of the gains of the closed loop amplifiers U-1a and U-1b. Beside phase shifting, the feedback capacitors C-1 and C-2 also provide a high frequency roll-off to minimize the effect of high harmonics of the vibrating transducer 10 or the effect of resonances of the transducer assembly members, viz. resonance of the rod 18 or crossbar 22.

Capacitor C-3 provides DC isolation between amplifiers U-1a and U-1b; also, capacitor C-4 provides DC isolation from U-1b to U-4. Resistors R-5 and R-8 are DC ground returns necessary when the amplifiers U-1a and U-1b are AC coupled. Capacitor C-6 at TP 1 provides additional isolation from stray high frequency electromagnetic signals picked up by the detector coil 2 from electrical machinery operating nearby.

The gain controlled operational amplifiers U-1a and U-1b and operational amplifier U-4 with bipolar transistors Q-11 and Q-12 and junction field effect transistors Q-1, Q-2 and Q-10 provides an accurately controllable voltage gain which is variable over an extremely wide dynamic range of greater than 200,000:1. To prevent possible distortion by transistors Q-1 and Q-2, the output voltage level of detector coil 2 is maintained by proper gap adjustment of the coil 2 and crossbar pole piece 25 and also by proper selection of the precision temperature compensated reference voltage and temperature stable resistors R-28 and R-29, which set the precise level for the amplitude of the crossbar 22, which is approximately 50 microns peak-to-peak (25 microns peak).

In order to provide the gain control voltage at the gates of FETs Q-1 and Q-2, the signal generated by the electromagnetic interaction of the vibrating transducer crossbar 22 and the detector coil 2 is applied to the first stage of the operational amplifier U-2. The gain of this amplifier is set by resistors R-12 and R-13; high frequency roll-off is provided by capacitor C-7.

The output of U-2a is AC coupled via C-8 and R-14 to the input of U-2b, the gain of which is preset by feedback resistor R-16 and ground return resistor R-15. The output of U-2b is sampled and held by sample-and-hold amplifier U-3 to establish the correct gain of the servo control amplifier U-1, U-4. Electrical noise in the system is largely the product of the servo system hunting for the correct null, which was inherent in the circuit disclosed in FIG. 8 of U.S. Pat. No. 3,762,429. Drift stabilization by capacitor C134a and associated resistor R134b (also clamping diode 115 and the time constant network comprised of C-114 and R-113) in the aforementioned patent resulted in somewhat sluggish control operation of the gain control bus. Therefore, an improved sample-and-hold technique was applied through the second stage of operational amplifier U-2 via U-5, a comparator, and by U-6, a monostable multivibrator.

The amplified signal of the detector coil 2 is sampled once per cycle by the comparator circuit U-5 which switches at a precise voltage level. The output of U-5 is differentiated for precise timing by capacitor C-10 and resistor R-19. The resulting pulse triggers a monostable multivibrator U-6. Diode clamps D-3 and D-4 select the negative trigger pulse from the differentiator circuit C-10, R-19 for correct firing of the 555 multivibrator.

The 555 integrated circuit U-6 is a well-known integrated circuit (IC) made for timing applications by Motorola and other IC manufacturers. In this circuit, its supply voltage is zero (ground) on the positive terminals 4 and 8, and $-12$ volts on the negative terminal 1. The circuit is wired to generate a 100 microsecond pulse at pin 3 for each trigger pulse at pin 2. Since the supply voltage to U-6 (the 555) is negative, the output is normally at the negative rail until a pulse is generated. At that time, pin 3 rises to 0 volts for 100 microseconds. The 100 microsecond time constant is determined by R-20 and C-12.

Negative biasing of U-6 is convenient for switching Q-3, the sample-and-hold switch. When the gate of Q-3 is negative, its drain-source resistance is extremely high; the switch is open. As the output of U-6 is pulsed to 0 volts, Q-3 is turned on; the drain-source resistance approaches a minimum near 200 ohms, and the signal charges the hold capacitor C-14. Timing of this circuit is such that each cycle is sampled on the same phase of the signal.

The AC voltage output of the second stage of operational amplifier U-2 is coupled to the comparator U-5 through a 90° phase shift network comprising resistor R-17 and capacitor C-9. The time constant of this network is selected to be sufficiently long so that approximately 90° phase shift is obtained at the fundamental torsional frequency of the vibrating transducer driven by the drive coil 1. Since this 90° phase shift is correct only for the fundamental torsional mode, lower or higher frequency resonances are not transmitted through the phase shifter, thus eliminating automatic lock-in of the control loop to other frequencies. The driver coil acts through the pole pieces so that a smooth sinusoidal excursion is obtained which is synchronized with the transducer's natural torsional period of oscillation. This smooth transducer action provides the detector coil 2 with a synchronous magnetic field variation resulting in a clean sinusoidal detector coil signal. A smooth voltage signal is important since the detector signal provides the precision control for the subsequent circuit.

As a result of the action of the aforementioned phase shift network, the AC voltage waveform at the inverting input of U-5 has a zero crossover which corresponds to peaks of the AC waveform of the voltage developed at the output of amplifier U-2. The integrated comparator U-5 converts the sinusoidal waveform to a square wave, the transistions of which occur at times corresponding to the zero crossovers of the voltage waveform appearing at the output of U-2. The application of U-5 (CA-3130) eliminates a large part of the circuit described in U.S. Pat. No. 3,762,429, FIG. 3; namely, Q-11, Q-12, Q-4, Q-5, diodes 144 to 146 and other associated resistors and capacitors. Furthermore, it provides precise operation parameters.

The pulses developed by integrated circuits U-5 and U-6 are applied to the gate of the sampling junction field effect transistor Q-3, which is periodically conductive between its source and drain at times corresponding to peaks in the waveform at the output of amplifier U-2.

The sample-and-hold amplifier U-3 is a multifunction circuit. First, it samples the AC feedback from the detector coil at the positive peak. Second, it rectifies the AC signal and stores only the positive peak voltage on the hold cycle. Third, the precise reference voltage applied to the non-inverting input of U-3 sets the precise level of amplitude to be sustained by the transducer 10. A clamp is provided which prevents the sample-and-hold amplifier from being driven out of control and possibly latching under overload conditions.

The second stage output of operational amplifier U-2 switches into the inverting input of sample-and-hold circuit U-3 via R-22 and Q-3, an N channel field effect transistor, when the gate of Q-3 is triggered on by the pulse supplied through the one-shot circuit U-6 and its associated circuits.

The output of second stage U-2 is a pure sine wave having a frequency determined by the resonant frequency of the transducer 10. This AC signal is sampled on the positive peak of the cycle by the timing of the phase shifted pulse from U-6. The peak voltage is stored in C-14, a high quality hold capacitor which connects between the output and the inverting input of the sample-and-hold amplifier U-3. The sample-and-hold amplifier U-3 operates in the inverting mode with its gain set by R-23 and R-24. Diode D-1 clamps transients which create errors in the sample-and-hold amplifier U-3 at low voltage levels.

Figure 5:
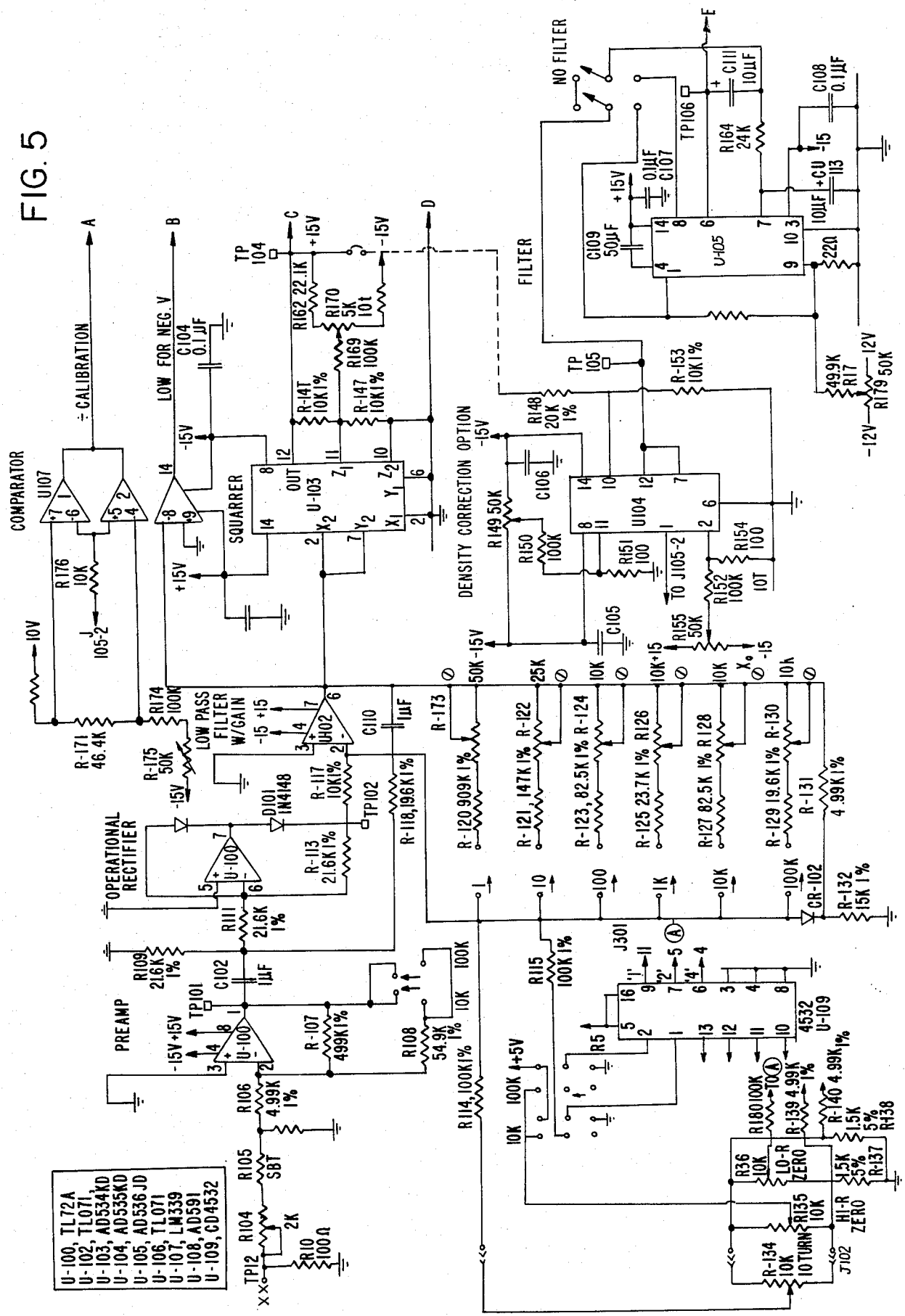
FIG. 5 is a functional schematic diagram of the portion of said viscometer that determines viscosity.

As shown in FIG. 5, the driver coil current is sampled by series resistor 34. This voltage is amplified by U-100a, rectified by U-100b, filtered by U-102 and "squared" by U-103 for an analog of power used to drive the transducer. The basis for the squaring circuit is that transducer driving power is proportional to the square of the current which is being sampled.

Amplifier U-100a is used to improve the signal-to-noise ratio for more accurate detection by the operational rectifier U-100b. The gain of U-100a is established by R-107, and the feedback resistor and input resistors R-104 and R-106. R-104 establishes the gain of the system at a single point which is true for all ranges; thus, this is essentially a single point calibration and not the multipoint procedure suggested in U.S. Pat. Nos. 3,712,117 and 3,762,429. On the highest ($\times 10^4$ and $\times 10^5$) ranges, the gain of the preamplifier U-100a is reduced in order not to clip the output.

Amplifier U-100b, diodes D-100 and D-101 and resistors R-111, R-113, R-117 and R-118 form an averaging operational rectifier which converts the AC signal coming from U-100a through C-102 to a pulsating DC signal which is fed to U-102, a low pass filter with gain. Gain adjustments for U-102 are provided for each range by the appropriate feedback resistor which is switched to U-102. For example, on range 1, the feedback resistor consists of R-120 and R-173. R-117 is the input resistor. A zero setting for the amplifier is needed in order to obtain accuracy. This is a DC level applied to the inverting input of U-102. The gain change of preamplifier U-100a requires a different zero point on the highest two ranges. Additional zeroing inputs are fed to the negative input of U-102 and are appropriately switches according to the range used.

The output of filter U-102 is fed to variable exponent amplifier U-103, with the output of U-103 being coupled to density correction divider U-104.

The inherent noise of a pipeline invariably requires special filtering to permit the precision readings which are possible with the viscometer of the present invention. An active filter is almost always necessary for in-line applications. A compact and fast filter has been devised from a monolithic RMS to DC converter, U-105, which accurately averages the irregular waveform which it receives as an input.

An error is introduced by the RMS-DC converter U-105 in that system and line noise are added to the output rather than averaged to zero, as would be desirable. To correct this problem, an offset which is equivalent to the system noise is injected into the converter U-105 by variable resistor R-179. The active filter time constant is set by selection of C-109. Other active filters could be used, but would be slower in response.

Various electronic switching features are incorporated in the digital display, which (along with any recorder or data bus) receives input signals on lines A, B, C, D and E. Included are the ability to read viscosity and temperature, or to alternate the readings. When temperature is read, the display exponent lights as a "C" or "F" for the appropriate temperature system and the display annunciator light changes from "Viscosity" to "Temperature". Other display annunciators which indicate the calibration status of the density correction, are turned off when temperature is displayed.

In the viscosity display mode, binary data from the front panel range switch, via U-109, is fed directly to the display, which displays the proper viscosity range exponent. If the exponent is zero, the display is blanked. This is accomplished by a resistor-transistor "AND" gate which drives the blanking input to the display "low" if any bit is high. When all bits are low, the blanking input goes high and the display is turned off. In the temperature display mode, the display inputs are pre-wired for either "C." (Celsius) or "F." (Fahrenheit).

Annunciators are provided for an indication of when the density correction is being used.

Industrial control systems frequently use an analog current output rather than the conventional voltage output when the data is to be transmitted over long lines via a data bus. The advantage of the current output system is that losses in the wire are compensated no matter what its length. The noise which is picked up on long lines is also minimized by the current output system.

We claim:

1. A transducer assembly for a torsional mode rotational vibratory viscometer, comprising:
    a metal support plate having opposed lower and upper surfaces and a hole extending through the plate from said lower surface to said upper surface;
    a hollow cylindrical metal sheath having torsional elasticity, the outer surface of an upper end part of said sheath extending through said hole from said upper surface to said lower surface and protruding from said lower surface, said sheath being secured to said plate at said hole by metal welds at both of said surfaces, so that said sheath is substantially coaxial with said hole;
    an immersible tip member secured to a lower end part of said sheath below said plate;
    a rigid cylindrical metal rod disposed within, spaced from and substantially coaxial with said sheath, a lower end part of said rod being secured to the lower end part of said sheath by a metal weld;
    said rod extending through said hole and having an upper end above said plate; and
    a metal crossbar secured to the upper end of said rod, said crossbar comprising magnetically permeable means.

2. The transducer assembly according to claim 1, wherein said sheath, rod, and the material of said welds comprise the same metal.

3. The transducer assembly according to claim 2, wherein said material is steel.

4. The transducer assembly according to claim 3, wherein said steel comprises stainless steel, 316 stainless steel alloy, 321 stainless steel alloy, 324 stainless steel alloy, or 329 stainless steel alloy.

5. The transducer assembly according to claim 1, wherein said crossbar comprises a relatively non-magnetic hollow cylindrical steel member having magnetically permeable pole pieces adjacent the ends of said hollow member.

6. The transducer assembly according to claim 1, further comprising:
    a drive coil adjacent one end of said crossbar for applying magnetic force thereto to cause rotational oscillation of said crossbar, rod, tip and sheath;
    a magnetic detector coil adjacent the other end of said crossbar to detect said oscillation;
    first circuit means connected between said coils to maintain said oscillation at substantially the natural frequency thereof and at a predetermined constant amplitude; and
    second circuit means for generating a viscosity-density product indicating signal corresponding to the power supplied to said drive oil.

7. The transducer assembly according to claim 6, wherein said first circuit means includes a sample-and-hold circuit for sampling an input signal corresponding to the output of said detector coil at a given part of each cycle of said oscillation, said sample-and-hold circuit including means for clipping the input signal thereto at a level proportional to the amplitude to said oscillation.

8. The transducer assembly according to claim 6 or 7, wherein said second circuit means includes a variable exponent amplifier for converting a processed signal corresponding to the current supplied to said drive coil, to said viscosity-density product indicating signal.

9. The transducer assembly according to claim 8, wherein said variable exponent amplifier has an exponent range on the order of 1.9 to 2.1.

10. The transducer assembly according to claim 8, wherein said second circuit means includes an RMS to DC converter for filtering the output of said variable exponent amplifier.

11. The transducer assembly according to claim 6, wherein said first circuit means includes means for adjusting the phase shift between the output signal from said detector coil and the input signal to said drive coil, to compensate for transmission line length variations between said coils and said first circuit means.

12. A rotational vibratory viscometer transducer and circuit, comprising:
a transducer assembly comprising:
a metal support plate having opposed lower and upper surfaces and a hole extending through the plate from said lower surface to said upper surface,
a hollow cylindrical metal sheath having torsional elasticity, the outer surface of an upper end part of said sheath extending through said hole from said upper surface to said lower surface and protruding from said lower surface, said sheath being secured to said plate at said hole by metal welds at both of said surfaces, so that said sheath is substantially coaxial with said hole,
an immersible tip member secured to a lower end part of said sheath below said plate,
a rigid cylindrical metal rod disposed within, spaced from and substantially coaxial with said sheath, a lower end part of said rod being secured to the lower end part of said sheath,
said rod extending through said hole and having an upper end above said plate, and
a metal crossbar secured to the upper end of said rod, said crossbar comprising magnetically permeable means;
a drive coil adjacent one end of said crossbar for applying magnetic force thereto to cause rotational oscillation of said crossbar, rod, tip and sheath;
a magnetic detector coil adjacent the other end of said crossbar to detect said oscillation;
first circuit means connected between said coils to maintain said oscillation at substantially the natural frequency thereof and at a predetermined constant amplitude,
said first circuit means including a sample-and-hold circuit for sampling an input signal corresponding to the output of said detector coil at a given part of each cycle of said oscillation; and
second circuit means for generating a viscosity-density product indicating signal corresponding to the power supplied to said drive coil.

13. The transducer and circuit according to claim 12, wherein said second circuit means includes a variable exponent amplifier for converting a processed signal corresponding to the current supplied to said drive coil, to said viscosity-density product indicating signal.

14. The transducer and circuit according to claim 13, wherein said variable exponent amplifier has an exponent range on the order of 1.9 to 2.1.

15. The transducer and circuit according to claim 12 or 13, wherein said second circuit means includes an RMS to DC converter for filtering the output of said variable exponent amplifier.

16. The transducer and circuit according to claim 12 or 13, wherein said first circuit means includes means for adjusting the phase shift between the output signal from said detector coil and the input signal to said drive coil, to compensate for transmission line length variations between said coils and said first circuit means.

17. A rotational vibratory viscometer transducer and circuit, comprising:
a transducer assembly comprising:
a metal support plate having opposed lower and upper surfaces and a hole extending through the plate from said lower surface to said upper surface,
a hollow cylindrical metal sheath having torsional elasticity, the outer surface of an upper end part of said sheath extending through said hole from said upper surface to said lower surface and protruding from said lower surface, said sheath being secured to said plate at said hole by metal welds at both of said surfaces, so that said sheath is substantially coaxial with said hole,
an immersible tip member secured to a lower end part of said sheath below said plate,
a rigid cylindrical metal rod disposed within, spaced from and substantially coaxial with said sheath, a lower end part of said rod being secured to the lower end part of said sheath,
said rod extending through said hole and having an upper end above said plate, and
a metal crossbar secured to the upper end of said rod, said crossbar comprising magnetically permeable means;
a drive coil adjacent one end of said crossbar for applying magnetic force thereto cause rotational oscillation of said crossbar, rod, tip and sheath;
a magnetic detector coil adjacent the other end of said crossbar to detect said oscillation;
first circuit means connected between said coils to maintain said oscillation at substantially the natural frequency thereof and at a predetermined constant amplitude,
said first circuit means including a sample-and-hold circuit for sampling an input signal corresponding to the output of said detector coil at a given part of each cycle of said oscillation; and
second circuit means for generating a viscosity-density product indicating signal corresponding to the power supplied to said drive coil, said second circuit means including a variable exponent amplifier for converting a processed signal corresponding to the current supplied to said drive coil, to said viscosity-density product indicating signal.

18. The transducer and circuit according to claim 17, wherein said variable exponent amplifier has an exponent range on the order of 1.9 to 2.1.

19. The transducer and circuit according to claim 17 or 18, wherein said sample-and-hold circuit includes means for clipping the input signal thereto at a level proportional to the amplitude of said oscillation.

20. A rotational vibratory viscometer transducer and circuit, comprising:
a transducer assembly comprising:
a metal support plate having opposed lower and upper surfaces and a hole extending through the plate from said lower surface to said upper surface,
a hollow cylindrical metal sheath having torsional elasticity, the outer surface of an upper end part of said sheath extending through said hole from said upper surface to said lower surface and protruding from said lower surface, said sheath being secured to said plate at said hole by metal welds at both of said surfaces, so that said sheath is substantially coaxial with said hole, an immersible tip member secured to a lower end part of said sheath below said plate, a rigid cylindrical metal rod disposed within, spaced from and substantially coaxial with said sheath, a lower end part of said rod being secured to the lower end part of said sheath, said rod extending through said hole and having an upper end above said plate, and a metal crossbar secured to the upper end of said rod, said crossbar comprising magnetically permeable means;

a drive coil adjacent one end of said crossbar for applying magnetic force thereto to cause rotational oscillation of said crossbar, rod, tip and sheath;

a magnetic detector coil adjacent the other end of said crossbar to detect said oscillation;

first circuit means connected between said coils to maintain said oscillation at substantially the natural frequency thereof and at a predetermined constant amplitude, said first circuit means including:

a sample-and-hold circuit for sampling an input signal corresponding to the output of said detector coil at a given part of each cycle of said oscillation, said sample-and-hold circuit including means for clipping the input signal thereto at a level proportional to the amplitude of said oscillation, and means for adjusting the phase shift between the output signal from said detector coil and the input signal to said drive coil, to compensate for transmission line length variations between said coils and said first circuit means;

second circuit means for generating a viscosity-density product indicating signal corresponding to the power supplied to said drive oil, said second circuit means including:

a variable exponent amplifier for converting a processed signal corresponding to the current supplied to said drive coil, to said viscosity-density product indicating signal, and an RMS to DC converter for filtering the output of said variable exponent amplifier.

\* \* \* \* \*